(12) United States Patent
Huo et al.

(10) Patent No.: US 11,993,527 B2
(45) Date of Patent: May 28, 2024

(54) IMMOBILIZED MICROBIAL AGENT FOR IN SITU RESTORATION OF CONTAMINATED SEDIMENTS, PREPARATION METHOD AND APPLICATION THEREOF

(71) Applicant: CHINESE RESEARCH ACADEMY OF ENVIRONMENTAL SCIENCES, Beijing (CN)

(72) Inventors: Shouliang Huo, Beijing (CN); Jingtian Zhang, Beijing (CN); Beidou Xi, Beijing (CN); Chunzi Ma, Beijing (CN); Xiaochuang Li, Beijing (CN)

(73) Assignee: CHINESE RESEARCH ACADEMY OF ENVIRONMENTAL SCIENCES, Beijing (CN)

( * ) Notice: Subject to any disclaimer, the term of this patent is extended or adjusted under 35 U.S.C. 154(b) by 846 days.

(21) Appl. No.: 17/039,883

(22) Filed: Sep. 30, 2020

(65) Prior Publication Data
US 2021/0017058 A1    Jan. 21, 2021

Related U.S. Application Data

(63) Continuation-in-part of application No. PCT/CN2018/090736, filed on Jun. 12, 2018.

(30) Foreign Application Priority Data

May 15, 2018    (CN) .......................... 201810459724.0

(51) Int. Cl.
*C12M 1/00*    (2006.01)
*C02F 3/34*    (2023.01)
(Continued)

(52) U.S. Cl.
CPC .............. *C02F 3/34* (2013.01); *C02F 11/008* (2013.01); *C02F 11/02* (2013.01); *C12N 1/20* (2013.01); *C02F 2103/007* (2013.01)

(58) Field of Classification Search
CPC ..... C12N 1/20; C02F 11/008; C02F 2103/007
See application file for complete search history.

(56) References Cited

U.S. PATENT DOCUMENTS

| 5,695,541 A | * | 12/1997 | Kosanke | ................ | A01N 63/20 |
| | | | | | 71/7 |
| 2010/0062515 A1 | * | 3/2010 | Yamamoto | ............. | C12Q 1/045 |
| | | | | | 435/253.6 |

(Continued)

FOREIGN PATENT DOCUMENTS

| CN | 107151663 A | | 9/2017 |
| CN | 108060095 A | * | 5/2018 |
| WO | 00/39035 A1 | | 7/2000 |

OTHER PUBLICATIONS

English translation of CN 108060095 to Huang et al (generated 2024).*

(Continued)

*Primary Examiner* — Nathan A Bowers
(74) *Attorney, Agent, or Firm* — Seed IP Law Firm LLP

(57) ABSTRACT

An immobilized microbial agent for in situ restoration of contaminated sediments, composed of Hangjin clay 2 #-loaded conductive microorganisms, obtained by the following methods: 1) pretreating Hangjin clay 2 # to obtain particulate filler; 2) amplification culture of conductive microorganisms to a bacterial liquid to be inoculated, and adding the Hangjin clay 2 # pretreated in step 1 in a certain ratio, mixing under anaerobic conditions, removing the supernatant after standing, and obtaining the immobilized microbial agent; the conductive microorganisms are *Geobacter sulfurreducens*, *Geobacter metallireducens* and *Shewanella*. The invention also discloses a method for preparing the immobilized microbial agent and the application of in situ restoration of contaminated sediments.

10 Claims, 1 Drawing Sheet

(51) Int. Cl.
  *C02F 11/00*    (2006.01)
  *C02F 11/02*    (2006.01)
  *C12M 3/00*     (2006.01)
  *C12N 1/20*     (2006.01)
  *C02F 103/00*   (2006.01)

(56) References Cited

U.S. PATENT DOCUMENTS

2016/0073641 A1\* 3/2016 Allen .................. C12N 1/04
                                                504/117
2019/0183131 A1\* 6/2019 Kendirgi ............ A01N 63/22

OTHER PUBLICATIONS

International Search Report (with English Translation), dated Feb. 13, 2019, for International Application PCT/CN2018/090736. (9 pages).

Li et al., "In-Situ Control Technology of Phosphorus in Sediment of Eutrophic Lake" *Acta Hydrobiologica Sinica* 38(2):370-374, 2014. (15 pages—w/ English Translation).

\* cited by examiner

IMMOBILIZED MICROBIAL AGENT FOR IN SITU RESTORATION OF CONTAMINATED SEDIMENTS, PREPARATION METHOD AND APPLICATION THEREOF

CROSS-REFERENCES TO RELATED APPLICATIONS

This application is a continuation-in-part application of International Patent Application No. PCT/CN2018/090736, filed Jun. 12, 2018, which claims the benefit of Chinese Patent Application No. 201810459724.0, filed May 15, 2018, which applications are incorporated herein by reference in their entireties.

TECHNICAL FIELD

The present invention belongs to the field of water ecological restoration, and in particular relates to an immobilized microbial agent for in situ restoration of contaminated sediments.

The present invention also relates to a process for the preparation of the above materials.

The present invention also relates to the use of the above materials for the in situ restoration of contaminated sediments.

BACKGROUND

In recent years, with the country's emphasis on ecological environmental protection work, especially the implementation of Lake-chief system and River-chief system have effectively promoted the development of waterfront shoreline management, water pollution prevention, and water environment management. For lake ecosystems, exogenously input nutrients, after being partially degraded and absorbed into the water body, are mostly enriched in sediments and migrate and transform in water bodies and sediments under appropriate conditions. The management of lakes should focus on the improvement of water environmental quality and the removal of pollutants in sediments. Some domestic lake sediment management usually adopts the method of dredging mud, which can improve the water quality in a short period of time, but it has great damage to the habitat of the sediment which is difficult to recover.

In-situ coverage and restoration techniques are applied to separate the sediments from the upper body by placing one or more layers on the surface of the sediments, while using the chemical properties of the filler itself to interact with contaminants in the sediments to achieve removal of contaminants and the purpose of preventing nutrients from being released from the sediments to the water.

The in-situ coverage technology is mainly applied to some water bodies with low fluidity and weak hydrodynamic conditions. Initially, the natural materials such as sand and gravel are used to physically isolate the contaminated sediments and water bodies, afterward materials with certain adsorption properties and low price are developed slowly such as modified clay, bentonite, artificial zeolite, ash, geotextile. These materials can effectively reduce the content of organic matter in sediments. For example, in CN106277673A lake sediments is used as raw materials, then modified with zeolite and polyaluminum chloride, granulated and roasted to control the endogenous phosphorus loading of sediments; or in CN105923963A magnetic granular activated carbon is used as a covering material to fix the persistent organic pollutant in the sediments.

In recent years, the development of immobilized microbial agents has made microbial remediation of contaminated sediments a hot topic. For example, the strain is loaded with zeolite and coated with flocculant and then put into oil-contaminated waters. After one month, the oil degradation efficiency of most stations is above 50% (CN106698672A); using river sand and bioactive multilayer which synergistically combine fixed high-efficiency nitrifying bacteria, denitrifying bacteria and natural zeolites to reduce the release of contaminants into the water body (CN102531197A). However, the immobilized carrier used in the above technique only functions to adsorb bacteria, and cannot participate in the degradation process of microorganisms on organic matters, so that the degradation efficiency of the pollutants is limited.

In 2007, for the first time, scientists discovered the natural biogeobattery effect in marine sediments, that is, a process wherein electrons generated from microorganisms oxidize organic donors such as organic carbon and sulfide in the anaerobic region of sediments are transmitted to aerobic zone over long distances by extracellular mediators, then are subjected to a reduction reaction with electron acceptors such as oxygen in the overlying water which is spatially isolated. This extracellular electron transfer process is mainly achieved by microbial nanowires and cytochrome c. The microorganisms with similar structures are mainly *Bacillus* and *Shewanella*. However, how to apply this mechanism in the actual water environment and promote the degradation of various pollutants is an important challenge faced by current environmental microbiology and environmental engineering researchers.

SUMMARY

It is an object of the present invention to provide an immobilized microbial agent for in situ restoration of contaminated sediments.

It is still another object of the present invention to provide a method for preparing the above materials.

In order to achieve the above objects, the immobilized microbial agent for in situ restoration of contaminated sediments provided by the present invention is composed of Hangjin clay 2 # loaded with conductive microorganisms, and is obtained by the following method:

1) pretreating Hangjin clay 2 # to obtain particulate filler;

2) amplification culture of the conductive microorganisms to a bacterial liquid to be inoculated, and adding the Hangjin clay 2 # pretreated in step 1 in a certain ratio, mixing under anaerobic conditions, removing the supernatant after standing, and obtaining the immobilized microbial agent; wherein the conductive microorganisms are *Geobacter sulfurreducens, Geobacter metallireducens* and *Shewanella*.

In the immobilized microbial agent according to the present invention, the particle size of the Hangjin clay 2 # particulate filler is less than 0.15 mm.

In the immobilized microbial agent according to the present invention, 15-20 g of Hangjin clay 2 # is added per 30 ml of the bacterial liquid to obtain an immobilized microbial agent having a bacterial adsorption rate of ≥90%.

The present invention further provides a method for preparing the immobilized microbial agent according to the present invention, comprising:

1) pretreatment of Hangjin clay 2 # to obtain particulate filler;

2) amplification culture of the conductive microorganisms to a bacterial liquid to be inoculated, and adding the Hangjin clay 2 # pretreated in step 1 in a certain ratio, mixing under anaerobic conditions, removing the supernatant after standing, and obtaining the immobilized bacteria; wherein the conductive microorganisms are *Geobacter sulfurreducens*, *Geobacter metallireducens* and *Shewanella*.

In the method according to the present invention, the particle size of the Hangjin clay 2 # particulate filler is less than 0.15 mm.

In the method according to the present invention, 15-20 g of Hangjin clay 2 # is added per 30 ml of the bacterial liquid to obtain an immobilized microbial agent having a bacterial adsorption rate of ≥90%.

In the method according to the present invention, the pretreatment of Hangjin clay 2 # comprises: grinding the Hangjin clay 2 # through a 100 mesh sieve, adding $H_2SO_4$ to acidify at 90° C., and adjusting the pH to 7.5 with an alkali solution; centrifuging the product to remove the supernatant, washed with water, dried at 80-90° C., and fired at 700-800° C. to obtain a particulate filler having a particle diameter of less than 0.15 mm.

In the method according to the present invention, the amplification culture of the conductive microorganisms comprises:

1) in an anaerobic aseptic environment, smearing the three original strains of *Geobacter sulfurreducens*, *Geobacter metallireducens* and *Shewanella* respectively on a medium plate and placing in an anaerobic incubator at 25-30° C. to culture, and verifying the purity of the target bacteria;

2) inoculating the verified single colony onto the inclined surface of a solid medium, culturing at 25-30° C., and inoculating the liquid medium in an anaerobic aseptic environment, and culturing at 25-30° C., 200 r/min;

wherein the liquid medium comprises: 20 g/L NaCl, 0.77 g/L KCl, 0.25 g/L $NH_4Cl$, 0.1 g/L $KH_2PO_4$, 0.2 g/L $MgSO_4.7H_2O$, 1% DL vitamin, 1% DL mineral and 2.0 g/L $NaHCO_3$, wherein the electron acceptor is 12.25 g/L ferric citrate, and the electron donor is 0.6 g/L acetic acid; and 3) inoculating the above three kinds of bacterial liquids simultaneously into a fermenter with anaerobic culture at a dose of 2%-6%, wherein the culture conditions are: pH value is 7.0-7.5, temperature is 25-30° C., and oscillation speed is 150 r/min, when the cell density of the cells reaches $10^8$/mL or more, the culture is finished.

In the method according to the present invention, before the amplification culture of the conductive microorganisms, the oxygen in the liquid medium before sterilization is removed by using $N_2:CO_2$ in a volume ratio of 80:20, and then sterilized at 121° C. for 15 min.

The immobilized microbial agent according to the present invention can be used for the in situ restoration of contaminated sediments, wherein the immobilized microbial agent is inoculated into the sediments at a ratio of 0.5% to 5%, and the lake water filtered through a 0.45 μm filter membrane is added to decompose the contaminants in the sediments by the natural biogeobattery effect.

The significant effects of the present invention are:

When the immobilized microbial agent is applied to contaminated sediments it can increase the abundance of *Shewanella* and *Bacillus* in sediments and enhance the removal of organic pollutants. At the same time, using Hangjin clay 2 # as a carrier, the microorganisms can use the $Fe_2O_3$ as an electron acceptor to complete the extracellular electron transfer process, accelerate the reaction rate, and effectively improve the removal effect of pollutants.

DETAILED DESCRIPTION

The present invention is described in detail below.

The preparation method of the immobilized microbial agent of the invention comprises the following steps:

1) Pretreatment of Hangjin clay 2 #: Hangjin clay 2 # is coarsely crushed and ground with a mortar directly through a 100 mesh sieve, and acidified in a ratio of 1:10 (mass:volume) with 2.5 mol/L $H_2SO_4$ at 90° C. for 2 h; then added 5 mol/L NaOH solution to adjust the pH to 7.5. The mud water mixture is centrifuged and poured off the supernatant, washed 3-4 times with pure water, dried at 90° C., then put into the muffle furnace at 750° C. After being calcined at a high temperature of 750° C. for 3 hours, a particulate filler having a particle diameter of less than 0.15 mm is finally obtained.

2) Screening of strains: The microorganisms to be screened include *Geobacter sulfurreducens* strain DL1 (ATCC52573), *Geobacter metallireducens* (ATCC 53774), and *Shewanella oneidensis* strain MR-1 (ATCC 700500).

3) Separation and culture of strains: The frozen original strain is smeared on a sterilized and dried medium plate in an anaerobic aseptic environment, repeatedly streaked, and placed in an anaerobic incubator at 30° C. Under the culture, the presence or absence of bacteria was observed after 24 hours to verify the purity of the target bacteria. A single colony of the correct colony is picked up with a sterile inoculating loop, inoculated onto the inclined surface of the solid medium, and repeatedly streaked, and cultured at 30° C. for 72 hours. The above-mentioned strain on the inclined surface is inoculated into a liquid medium in an anaerobic aseptic environment, and cultured at 30° C., 200 r/min.

4) Mixing of strains: The above three kinds of bacterial liquids are simultaneously inoculated with anaerobic culture in a fermenter at an inoculation amount of 2% to 6%. The culture conditions are as follows: pH between 7.0 and 7.5, temperature at 30° C., and oscillation speed of 150 r/min. When the cell density reaches $10^8$ cells/mL or more, and the culture is completed.

5) Adsorption of immobilized microbial agent: The prepared Hangjin clay filler is mixed with the bacterial liquid in a certain proportion, and shaken in a shaker for 24 hours under anaerobic conditions. After standing for a period of time, the supernatant is poured off. Immobilized microbial agents with a bacterial adsorption rate of ≥90% is obtained.

Figure 1:
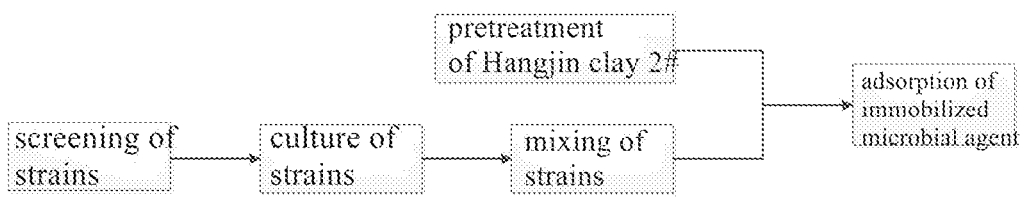
FIG. 1 is a process flow of an immobilized microbial agent of the present invention.

The process flow can be seen in FIG. 1.

Application method of immobilized microbial agent of the invention in the contaminated sediments is as follows:

The prepared immobilized microbial agent is inoculated into the sediments at a ratio of 0.5% to 5%, and the lake water filtered through the 0.45 μm filter membrane is added to decompose the contaminants in the sediments by the natural biogeobattery effect.

The present invention is described in detail below with reference to the accompanying drawings and specific embodiments, but the scope of the invention is not limited to the specific embodiments.

Example 1

1) Preparation of Hangjin Clay 2 # Load Matrix

Hangjin clay 2 # is a type of clay naturally present in the region of Hangjin Qi of the Ordos area in Inner Mongolia. The geographical origin of the term defines the unique composition of the clay, which is a porous material containing quartz, feldspar, calcite and amorphous iron oxide ($Fe_2O_3$).

The composition of Hangjin clay 2 # according to certain analytical tests comprises: $SiO_2$ 50.9 wt. %; $Al_2O_3$ 15.2 wt. %; CaO 6.4 wt. %; $Fe_2O_3$ 5.9 wt. %; MgO 3.6 wt. %; $K_2O$ 3.6 wt. %; $Na_2O$ 0.9 wt. %; $TiO_2$ 0.6 wt. %; and loss on ignition 12.9%. See also the analytic results of Hangjin clay 2 # described in CN1623651A1.

The commercial available Hangjin clay 2 # was coarsely crushed and ground through a 100 mesh sieve. 200 g of the ground Hangjin clay 2 # was weighed, then 2000 ml of 2.5 mol/L $H_2SO_4$ was added, and acidified in a water bath at 90° C. for 2 h. The pH was adjusted to 7.5 with a 5 mol/L NaOH solution. The mixture was poured into a centrifuge tube, centrifuged at 8000 rpm for 10 min. The supernatant was decanted, washed with pure water, and centrifuged again, repeating 3-4 times. The precipitate was placed in an oven and dried at 90° C. for 2 h, and then placed in a muffle furnace at a high temperature of 750° C. for 3 h to finally obtain about 190 g of particulate filler having a particle diameter of less than 0.15 mm.

2) Screening of Strains

In this example, three kinds of bacteria capable of using iron oxides, humus and the like as electron acceptors were selected from more than 30 kinds of extracellular electrogenic strains, and the selected strains included *Geobacter sulfurreducens* strain DL1 (ATCC52573, designated as T1), *Geobacter metallireducens* (ATCC 53774, designated as T2), and *Shewanella oneidensis* strain MR-1 (ATCC 700500, designated as T3).

3) Plate Purification, Slant Culture and Amplification Culture of the Strain.

① In an anaerobic aseptic environment, the three frozen original strains were inoculated into the sterilized LB solid medium plate by sterile inoculating loop, repeatedly streaked, and cultured at 30° C. in the anaerobic environment for 24 h. Observe the presence or absence of bacteria to verify the purity of the target bacteria.

Among them, the preparation method of the LB solid medium plate was: 10 g of tryptone, 5 g of yeast extract and 10 g of sodium chloride were weighed, respectively and dissolved in 1000 ml of pure water with stirring, stirred evenly, and the pH value was adjusted to 7.4 with NaOH. 1.5 g of agar powder was added to 100 ml of LB medium, and the mixture was boiled and dissolved, sterilized at 121° C. for 20 min, then the temperature was dropped to below 60° C. Every 15 ml of the resulting liquid was poured and laid flat on the bottom of the culture dish (d=9 cm). After cooling a solid medium plate was obtained.

② In an anaerobic aseptic environment, the verified single colony was picked up by a sterile inoculating loop, inoculated onto the inclined surface of LB solid medium, and repeatedly streaked, and cultured at 30° C. for 72 hours.

③ In an anaerobic aseptic environment, the colonies were picked from the plate by an inoculating loop into a 500 mL Erlenmeyer flask containing 200 mL of liquid medium, and cultured at 30° C., 200 r/min to a cell density of $10^8$/mL or more. Then the culture was stopped.

The composition of the liquid medium was 20 g/L NaCl, 0.77 g/L KCl, 0.25 g/L $NH_4Cl$, 0.1 g/L $KH_2PO_4$, 0.2 g/L $MgSO_4 \cdot 7H_2O$, 1% DL vitamin, 1% DL mineral and 2.0 g/L $NaHCO_3$; wherein the electron acceptor was 12.25 g/L ferric citrate, and the electron donor was 0.6 g/L acetic acid, and the pH was adjusted between 7.0-7.5.

4) Mixing of strains: In the anaerobic aseptic environment, the above three kinds of bacterial liquids were simultaneously inoculated into the liquid medium of the fermenter at a dose of 2% to 6%, and the culture was expanded in a water bath oscillator. The culture conditions were as follows: the temperature was 30° C. and the oscillation speed was 150 r/min. The cell density was increased to $10^8$ cells/mL or more.

The fermenter was made of borosilicate glass, which can withstand large pressure. It was wrapped with tin foil to protect it from light. The fermenter had a volume of 2.5 L, and 1.5 L liquid medium was added to it, and $N_2:CO_2$ (80:20, volume ratio) was used to purge it for 15 min. After the end of the aeration, the cans were sealed with a butyl rubber stopper and sterilized at 121° C. for 20 min.

5) Adsorption of Immobilized Microbial Agent:

In this example, the prepared Hangjin clay filler was mixed with the bacterial liquid in different proportions, and the specific ratio was shown in Table 1. The mixture was shaken under anaerobic conditions for 24 hours in a shaker, and after standing for a while, the supernatant was decanted, and finally the immobilized microbial agent having a cell adsorption rate of 90% was obtained by screening.

It can be seen from Table 1 that in each group of experiments, the adsorption rates of Hangjin clay 2 # on the three bacterial liquids were similar. With the increase of the amount of Hangjin clay 2 #, the adsorption rate of three kinds of bacterial liquids by Hangjin clay 2 # increased. Among them, the adsorption rate of the three kinds of bacterial liquids in the seventh group of Hangjin clay 2 # was the highest. When 30 ml of bacterial liquid was mixed with 15 g Hangjin clay 2 #, the ratio of Hangjin clay 2 # was 33.33% (the ratio of bacterial liquid to Hangjin clay 2 # was 2:1). After anaerobic oscillation for 24 h, the adsorption rate of Hangjin clay 2 # was the highest. The adsorption rate to T1 was 93.8%, the adsorption rate to T2 was 92.2%, and the adsorption rate to T3 was 91.3%. After the increase of the amount of Hangjin clay 2 #, the adsorption rate no longer increased.

6) Inoculation of Immobilized Microbial Agent:

In this example, the prepared immobilized microbial agent was inoculated into the sediments at a ratio of 0.5% to 5%, and the lake water filtered through the 0.45 μm filter membrane was added to degrade the pollutant in the sediments by using the natural biogeobattery effect.

Collect lake sediments and lake water with high nutrient content in the sediments, filter the sediments with a stainless steel sieve having a pore size of 1 mm, remove coarse particles such as dead branches, leaves and gravel, and filter the lake water with 0.45 μm filter to remove the suspension and algae. In five 7.5-liter jars (caliber 10.4 cm, height 34 cm, diameter 20.7 cm), 2.5 kg of sediments (filling height of about 8 cm) and 2.2 L of lake water (water body height of about 7 cm) were added, respectively, then cultured in an artificial atmospheric phenomena simulator at 30° C. for 30 days. Before the addition of the lake water, the immobilized microbial agent were added to the sediments in an amount of 0.0 g, 12.5 g, 25.0 g, 50.0 g, and 125.0 g (inoculation ratios were 0.0%, 0.5%, 1%, 2%, and 5%, respectively), stirring well with a glass rod. After the end of the reaction cycle, sediments at 0-2 cm depth, 2-4 cm depth and below 4 cm were collected with a sterile sampler, and the contents of TN, TP and TOC in the sediment were determined.

Result:

As shown in Table 2, at the initial stage of inoculation, the sediment TN, TP and TOC of the five jars were between 5461-5643 mg/kg, 1560-1723 mg/kg and 15.34-17.56 g/kg, respectively. Due to that the bacterial liquid contains certain C, N, and P, with the increase of the inoculation ratio, the contents of TN, TP, and TOC in the sediment increase slightly.

After 30 days of culture, the TP content of sediments at 0-2 cm depth is between 1496-1619 mg/kg, the TP content of sediments at 2-4 cm depth was between 1502-1622 mg/kg, and the TP content of sediments below 4 cm was between 1500-1624 mg/kg. Compared with the 0d, the difference of TP contents of sediments at different depths was smaller, mainly because a small part of phosphorus was released into the overlying water by the exchange interaction between sediment and water. Conductive microorganisms can decompose organic phosphorus in sediments into inorganic phosphorus under anoxic conditions, but it does not reduce the total amount of phosphorus in the sediments.

Figure 2:
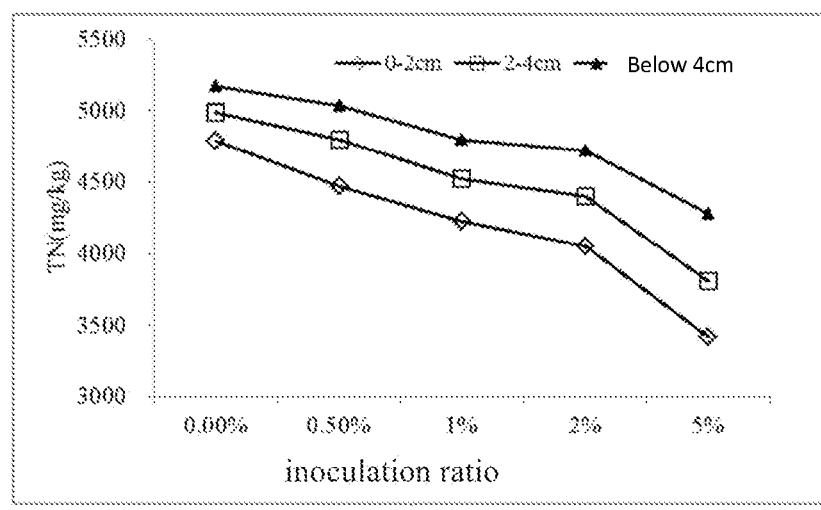
FIG. 2 is a graph of TN removal rate in sediments versus time.
Figure 3:
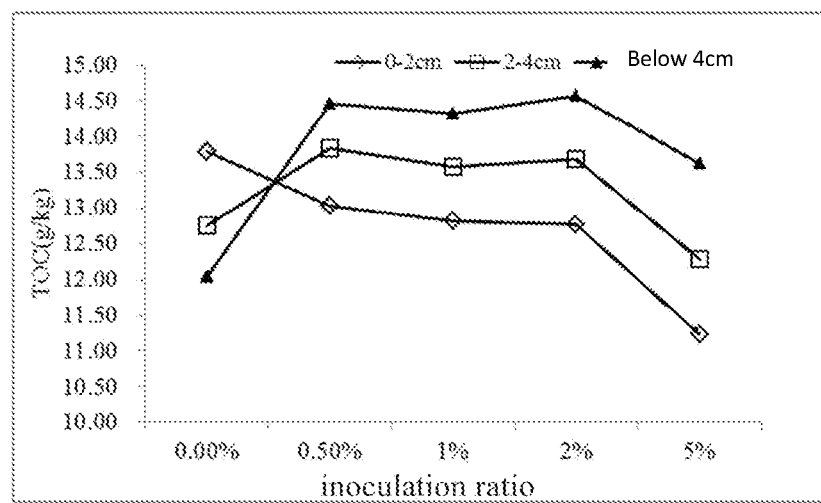
FIG. 3 is a graph of TOC removal rate in sediments versus time.

After 30 days of culture, the TN and TOC contents of sediments decreased in different degrees, and the results were shown in FIG. 2 and FIG. 3, respectively.

As shown in FIG. 2, after 30 days of culture, the TN removal rate of the blank group (0.00% inoculation ratio) ranged from 5.38% to 12.34%, indicating that the microorganisms in the sediment itself can also decompose and utilize the organic nitrogen compounds in the sediment under the anoxic condition, and denitrification reaction occurs to reduce the TN content of the sediment. With the increase of the inoculation ratio, the TN removal rate of the sediment increased gradually. When the inoculation ratio was 5%, the TN content of the sediment decreased fastest. After 30 days, the TN content of the sediment was between 3419-4280 mg/kg, and the TN removal rate ranged from 24.15% to 39.42%. At each inoculation ratio, the TN content of sediment at the 0-2 cm depth was the lowest, significantly lower than the TN content of the sediment at 2-4 cm depth and below 4 cm, indicating that the conductive microorganisms in the sediment in the surface layer can utilize the organic matter in a shorter distance from the sediment to react with the dissolved oxygen in the overlying water. It is helpful to increase the degradation efficiency of the surface sediment TN. As shown in FIG. 3, after 30 days of cultivation, the TOC content of the sediment was also reduced, showing a similar change law to the sediment TN. When the inoculation ratio was 5%, the TOC reduction of sediment was the largest, and the reduction rate was 22.39%-35.98%, which was reduced from 17.56 g/kg before inoculation to 11.24-13.63 g/kg.

Conclusion: It can be seen from the above embodiments that the material for in situ restoration of contaminated sediments of the present invention can effectively improve the removal effect of carbon and nitrogen in sediments, and is suitable for the repair of contaminated sediments.

TABLE 1

Adsorption effect of mixed bacteria liquid by Hangjin clay 2#

| Group | bacteria liquid (mL) | Hangjin clay 2# (g) | Hangjin clay 2#, ratio | adsorption rate to T1 | adsorption rate to T2 | adsorption rate to T3 |
|---|---|---|---|---|---|---|
| 1 | 30 | 2.0 | 6.25% | 34.7% | 36.3% | 35.6% |
| 2 | 30 | 3.0 | 9.09% | 45.3% | 46.5% | 44.9% |
| 3 | 30 | 6.0 | 16.67% | 55.1% | 53.7% | 56.6% |
| 4 | 30 | 8.0 | 21.05% | 61.9% | 60.6% | 62.5% |
| 5 | 30 | 10.0 | 25.00% | 77.3% | 76.6% | 75.1% |
| 6 | 30 | 12.0 | 28.57% | 85.1% | 84.8% | 87.2% |
| 7 | 30 | 15.0 | 33.33% | 93.8% | 92.2% | 91.3% |
| 8 | 30 | 20.0 | 40.00% | 90.5% | 91.3% | 90.2% |
| 9 | 30 | 22.0 | 44.00% | 89.2% | 90.5% | 88.7% |

TABLE 2

TN, TP and TOC contents in sediments at different inoculation ratios before inoculation

| Group | inoculation ratio | TN(mg/kg) | TP(mg/kg) | TOC(mg/kg) |
|---|---|---|---|---|
| 1 | 0.00% | 5461 | 1560 | 15.34 |
| 2 | 0.50% | 5495 | 1585 | 15.75 |
| 3 | 1.00% | 5526 | 1609 | 16.38 |
| 4 | 2.00% | 5580 | 1646 | 17.05 |
| 5 | 5.00% | 5643 | 1723 | 17.56 |

The invention claimed is:

1. An immobilized microbial agent for in situ restoration of contaminated sediments, composed of a Hangjin clay 2 # particular filler-loaded with conductive microorganisms, obtained by the following method:
   pretreating the Hangjin clay 2 # to obtain the particulate filler, the Hangjin clay 2# comprising quartz, feldspar, calcite and amorphous iron oxide;
   culturing and amplifying the conductive microorganisms to produce a bacterial liquid to be inoculated;
   adding the particulate filler into the bacteria liquid;
   mixing the particulate filler and the bacterial liquid under anaerobic conditions to provide a mixture; and
   removing a supernatant after letting the mixture stand, allowing solid and liquid phases to separate, thereby obtaining the immobilized microbial agents,
   wherein the conductive microorganisms include *Geobacter sulfurreducens*, *Geobacter metallireducens* and *Shewanella oneidensis*.

2. The immobilized microbial agent according to claim 1, wherein a particle size of the particulate filler is less than 0.15 mm.

3. The immobilized microbial agent according to claim 1, wherein 15-20 g of the particulate filler is added per 30 ml of the bacterial liquid to obtain the immobilized microbial agent having a bacterial adsorption rate of ≥at least 90%.

4. The use of the immobilized microbial agent of claim 1 for the in situ restoration of contaminated sediments, wherein the immobilized microbial agent was inoculated into the sediments at a ratio of 0.5% to 5%, and the lake water filtered through a 0.45 μm filter membrane is added to decompose the contaminants in the sediments by the natural biogeobattery effect.

5. A method for preparing an immobilized microbial agent, comprising the following steps:
   pretreating Hangjin clay 2 # to obtain a particulate filler, the Hangjin clay 2 # comprising quartz, feldspar, calcite and amorphous iron oxide;
   culturing and amplifying conductive microorganisms to produce a bacterial liquid to be inoculated and;
   adding the particulate filler proportionally into the bacterial liquid;

mixing the particulate filler and the bacterial liquid under anaerobic conditions to provide a mixture; and removing a supernatant from the mixture after letting the mixture stand, allowing solid and liquid phases to separate, thereby obtaining the immobilized microbial agent, wherein the conductive microorganisms are *Geobacter sulfurreducens, Geobacter metallireducens* and *Shewanella oneidensis*.

6. The method according to claim 5, wherein a particle size of the particulate filler is less than 0.15 mm.

7. The method according to claim 5, wherein 15-20 g of the particulate filler is added per 30 ml of the bacterial liquid to obtain the immobilized microbial agent having a bacterial adsorption rate of at least ≥90%.

8. The method according to claim 5, wherein pretreating the Hangjin clay 2 # comprises:
grinding the Hangjin clay 2 # to form clay particles,
sieving the clay particles through a 100 mesh sieve;
adding $H_2SO_4$ to the cay particles to acidify the clay particles at 90° C.;
adjusting a pH of the clay particles to 7.5 with an alkali solution;
centrifuging a mixture of the clay particles and the alkali solution to separate a supernatant from the neutralized clay particles;
removing the supernatant;
washing the clay particles with water;
drying the clay particles at a temperature ranging from 80 to 90° C.; and
firing the clay particles at a temperature ranging from 700 to 800° C., thereby obtaining the particulate filler having a particle size of less than 0.15 mm.

9. The method according to claim 5, wherein the culturing and amplifying the conductive microorganisms comprises:
1) in an anaerobic aseptic environment, smearing original strains of *Geobacter sulfurreducens, Geobacter metallireducens* and *Shewanella oneidensis*, respectively, on a medium plate, placing the medium plate in an anaerobic incubator at a temperature ranging from 25 to 30° C., culturing each of the original strains to produce a corresponding target bacteria, and verifying the purity of the corresponding target bacteria;
2) inoculating a single colony of the corresponding target bacteria onto an inclined surface of a solid medium, culturing the single colony at a temperature ranging from 25 to 30° C., inoculating the single colony into a liquid medium under an anaerobic aseptic environment, and culturing the single colony in the liquid medium at a temperature ranging from 25 to 30° C., and a vibration rate of 200 r/min;
wherein the liquid medium comprises: 20 g/L NaCl, 0.77 g/L KCl, 0.25 g/L $NH_4Cl$, 0.1 g/L $KH_2PO_4$, 0.2 g/L $MgSO_4·7H_2O$, 1% DL vitamin, 1% DL mineral and 2.0 g/L $NaHCO_3$, wherein 12.25 g/L ferric citrate is used as an electron acceptor, and 0.6 g/L acetic acid is used as an electron donor; and
3) inoculating each of the three bacterial liquids obtained from the respective original strains of *Geobacter sulfurreducens, Geobacter metallireducens* and *Shewanella oneidensis* simultaneously into a fermenter under an anaerobic aseptic environment at a dose of 2%-6% and culturing each of the bacterial liquids until a cell density of the bacteria reaches $10^8$/mL or more, wherein the culture conditions are: pH value of 7.0-7.5, temperature of 25-30° C., and oscillation speed of 150 r/min.

10. The method according to claim 9, further comprising:
before culturing and amplifying the conductive microorganisms, removing oxygen in the liquid medium by using a mixture of $N_2$ and $CO_2$ with $N_2$:$CO_2$ in a volume ratio of 80:20; and
sterilizing the liquid medium at 121° C. for 15 min.

* * * * *

UNITED STATES PATENT AND TRADEMARK OFFICE
CERTIFICATE OF CORRECTION

Page 1 of 2

PATENT NO. : 11,993,527 B2
APPLICATION NO. : 17/039883
DATED : May 28, 2024
INVENTOR(S) : Shouliang Huo et al.

It is certified that error appears in the above-identified patent and that said Letters Patent is hereby corrected as shown below:

In the Claims

Column 8, Claim 1, Line 32:
"the Hangiin clay" should read: --the Hangjin clay--.

Column 8, Claim 1, Line 41:
"microbial agents," should read: --microbial agent,--.

Column 8, Claim 3, Line 51:
"of ≥at least 90%." should read: --of at least 90%.--.

Column 8, Claim 5, Line 61:
"pretreating Hangjin clay" should read: --pretreating a Hangjin clay--.

Column 8, Claim 5, Line 62:
"the Hangiin clay" should read: --the Hangjin clay--.

Column 8, Claim 5, Line 65:
"inoculated and;" should read: --inoculated;--.

Column 9, Claim 7, Line 15:
"at least ≥90%." should read: --at least 90%.--.

Column 9, Claim 8, Line 18:
"form clay particles," should read: --form clay particles;--.

Column 9, Claim 8, Line 20:
"to the cay particles" should read: --to the clay particles--.

Signed and Sealed this
Seventeenth Day of December, 2024

Derrick Brent
*Acting Director of the United States Patent and Trademark Office*

CERTIFICATE OF CORRECTION (continued)
U.S. Pat. No. 11,993,527 B2

Column 9, Claim 9, Line 34:
"wherein the culturing" should read: --wherein culturing--.

Column 10, Claim 9, Line 15:
"medium comprises: 20 g/L" should read: --medium comprises 20 g/L--.